US010714215B2

(12) United States Patent
Bertram

(10) Patent No.: US 10,714,215 B2
(45) Date of Patent: *Jul. 14, 2020

(54) SYSTEM AND METHOD OF MONITORING AND CONFIRMING MEDICATION DOSAGE

(71) Applicant: 1070715 B.C. Unlimited Liability Company, Minnetonka, MN (US)

(72) Inventor: Carl Bertram, Downers Grove, IL (US)

(73) Assignee: 1070715 B.C. Unlimited Liability Company, Minnetonka, MN (US)

( * ) Notice: Subject to any disclaimer, the term of this patent is extended or adjusted under 35 U.S.C. 154(b) by 66 days.

This patent is subject to a terminal disclaimer.

(21) Appl. No.: 16/028,944

(22) Filed: Jul. 6, 2018

(65) Prior Publication Data

US 2018/0315497 A1 Nov. 1, 2018

Related U.S. Application Data

(63) Continuation of application No. 15/413,754, filed on Jan. 24, 2017, now Pat. No. 10,042,985, which is a
(Continued)

(51) Int. Cl.
*G16H 20/10* (2018.01)
*G06T 7/00* (2017.01)
(Continued)

(52) U.S. Cl.
CPC .............. *G16H 20/10* (2018.01); *G06F 19/00* (2013.01); *G06F 19/3462* (2013.01);
(Continued)

(58) Field of Classification Search
CPC ...... G16H 20/10; G16H 20/13; G06T 7/0012; G06T 7/0014; G06K 9/00885; G06K 9/00771; G06K 7/1413; G06Q 50/22
See application file for complete search history.

(56) References Cited

U.S. PATENT DOCUMENTS

| 2002/0059117 A1* | 5/2002 | Yoch | G06Q 30/06 705/27.1 |
| 2002/0163435 A1* | 11/2002 | Kosaka | G06F 19/326 340/573.1 |
| 2009/0138122 A1* | 5/2009 | Wagner | A61G 12/001 700/226 |
| 2009/0243833 A1* | 10/2009 | Huang | G06Q 10/087 340/505 |

(Continued)

OTHER PUBLICATIONS

Medication Administration Video, CSMD tube, https://www.youtube.com/watch?v=YXgrvZpH2Y0&t=4s, uploaded Aug. 17, 2010.*

*Primary Examiner* — John B Strege

(74) *Attorney, Agent, or Firm* — Seyfarth Shaw LLP; Brian Michaelis

(57) ABSTRACT

A medication monitoring system including a patient information unit having a processor, a memory and a patient monitoring unit and a program executing in the memory executing the steps of communicatively coupling a first device with a second device, transmitting live images from the first device to the second device, analyzing the content of the live images to identify at least one biometric attribute of a user in the image and at least one bar code on a container in the image, determining whether the bar code is associated with at least one biometric attribute, and notifying the user whether to consume the contents of the container based on the association of the bar code with the biometric attribute.

20 Claims, 6 Drawing Sheets

Related U.S. Application Data continuation of application No. 14/608,478, filed on Jan. 29, 2015, now Pat. No. 9,576,355.

(60) Provisional application No. 61/934,275, filed on Jan. 31, 2014.

(51) Int. Cl.
  *G06Q 50/22* (2018.01)
  *G06F 19/00* (2018.01)
  *G06K 7/14* (2006.01)
  *G06K 9/00* (2006.01)
  *G16H 20/13* (2018.01)

(52) U.S. Cl.
  CPC ....... *G06K 7/1413* (2013.01); *G06K 9/00771* (2013.01); *G06K 9/00885* (2013.01); *G06Q 50/22* (2013.01); *G06T 7/0012* (2013.01); *G06T 7/0014* (2013.01); *G16H 20/13* (2018.01)

(56) References Cited

U.S. PATENT DOCUMENTS

| | | | |
|---|---|---|---|
| 2010/0183199 A1* | 7/2010 | Smith | G06K 9/00597 382/117 |
| 2011/0015945 A1* | 1/2011 | Addy | G06F 19/3462 705/3 |
| 2011/0056290 A1* | 3/2011 | Bryant | G01F 23/292 73/293 |
| 2011/0268329 A1* | 11/2011 | Pronkine | G01F 23/0076 382/128 |
| 2012/0004770 A1* | 1/2012 | Ooyen | G07F 11/58 700/235 |
| 2013/0253291 A1* | 9/2013 | Dixon | A61G 7/018 600/323 |
| 2013/0261794 A1* | 10/2013 | Fauci | G06F 19/3462 700/237 |
| 2015/0061832 A1* | 3/2015 | Pavlovic | G07C 9/00158 340/5.83 |
| 2016/0089303 A1* | 3/2016 | Latorraca | G07F 11/62 312/209 |

\* cited by examiner

SYSTEM AND METHOD OF MONITORING AND CONFIRMING MEDICATION DOSAGE

RELATED APPLICATIONS

This application is a continuation of U.S. application Ser. No. 15/413,754 filed Jan. 24, 2017, which is a continuation of U.S. application Ser. No. 14/608,478 filed Jan. 29, 2015, which claims the benefit of and the priority from U.S. Provisional Application No. 61/934,275 filed Jan. 31, 2014.

BACKGROUND OF THE INVENTION

As the population ages, more and more people will find themselves requiring complicated therapies such as biotechnology self-injectable medications to manage/cure their disease or improve their quality of life. Many of the medications will require a user to become familiar with the clinical nature of the medications, how they interact with other medications they may be taking, how to store the medications and importantly how to inject themselves with a syringe to deliver the medication. The volume of information required to be learned is daunting. Injecting one's self with a needle may be an intimidating task that raises many questions on the proper method of injecting the syringe. A need exists for a method of facilitating patient knowledge associated with these complex therapies. A need exists also for facilitating and ease of use with unique and specialized healthcare services like confirming that the proper dosage of medication is injected into a user in the most effective area of the body.

SUMMARY OF THE INVENTION

One embodiment of the present invention includes a medication monitoring system including a patient information unit having a processor, a memory and a patient monitoring unit and a program executing in the memory executing the steps of communicatively coupling a first device with a second device, transmitting live images from the first device to the second device, analyzing the content of the live images to identify at least one biometric attribute of a user in the image and at least one bar code on a container in the image, determining whether the bar code is associated with at least one biometric attribute, and notifying the user whether to consume the contents of the container based on the association of the bar code with the biometric attribute.

Another embodiment includes the step of analyzing the content of the live image includes determining the contents of the container based on the bar code.

In another embodiment, a video is steamed from the first communication device to the second communication device if the contents of the container are associated with the user.

In another embodiment, the video includes instructions on how to properly administer the contents of the container.

In another embodiment, the contents of the container are a medication prescribed to the user.

In another embodiment, the medication is a liquid medication.

In another embodiment, the step of analyzing the contents of the live image includes the step of determining the level of the liquid medication in the container.

In another embodiment, the level of the liquid in the container is determined by identifying a line representing the top surface of the liquid in the container.

In another embodiment, the medication is a pill.

Another embodiment includes the step of analyzing the live image includes determining whether the proper amount of medication is withdrawn from the container by comparing levels before and after the medication is withdrawn.

Another embodiment of the present invention includes a medication monitoring system including a patient information unit having a processor, a memory and a patient monitoring unit and a program executing in the memory executing the steps of communicatively coupling a first device with a second device, transmitting live images from the first device to the second device, analyzing the content of the live images to identify at least one biometric attribute of a user in the image and at least one bar code on a container in the image, determining whether the bar code is associated with at least one biometric attribute, and notifying the user whether to consume the contents of the container based on the association of the bar code with the biometric attribute, providing information to the user on the proper method of preparing the contents of the vial for consumption, analyzing the content of the live images after notifying the user to determine whether the user has prepared the contents of the container for consumption, notifying the user of the user's compliance with the previously provided information.

In another embodiment, the information provided to the user includes a video depicting the preparation of the contents in the container for consumption.

Another embodiment includes the steps of providing instructions to the user relating to the proper administration of the contents of the container.

Another embodiment includes the step of analyzing the content of the live images to determine if the user is properly administering the contents of the container.

Another embodiment includes the step of notifying the user if the user is not properly administering the contents of the container.

In another embodiment, the notification includes providing information relating to correction actions the user can take to properly administer the contents of the container.

In another embodiment, the contents of the container are a liquid medication.

In another embodiment, the contents of the container are administered using a syringe.

In another embodiment, the medication must be administered to a specific location of the body.

In another embodiment, the step of analyzing the content of the live images to determine if the user is properly administering the contents of the container includes determining if the user is administering the liquid to the correct location of the body.

DETAILED DESCRIPTION OF THE INVENTION

Figure 1:
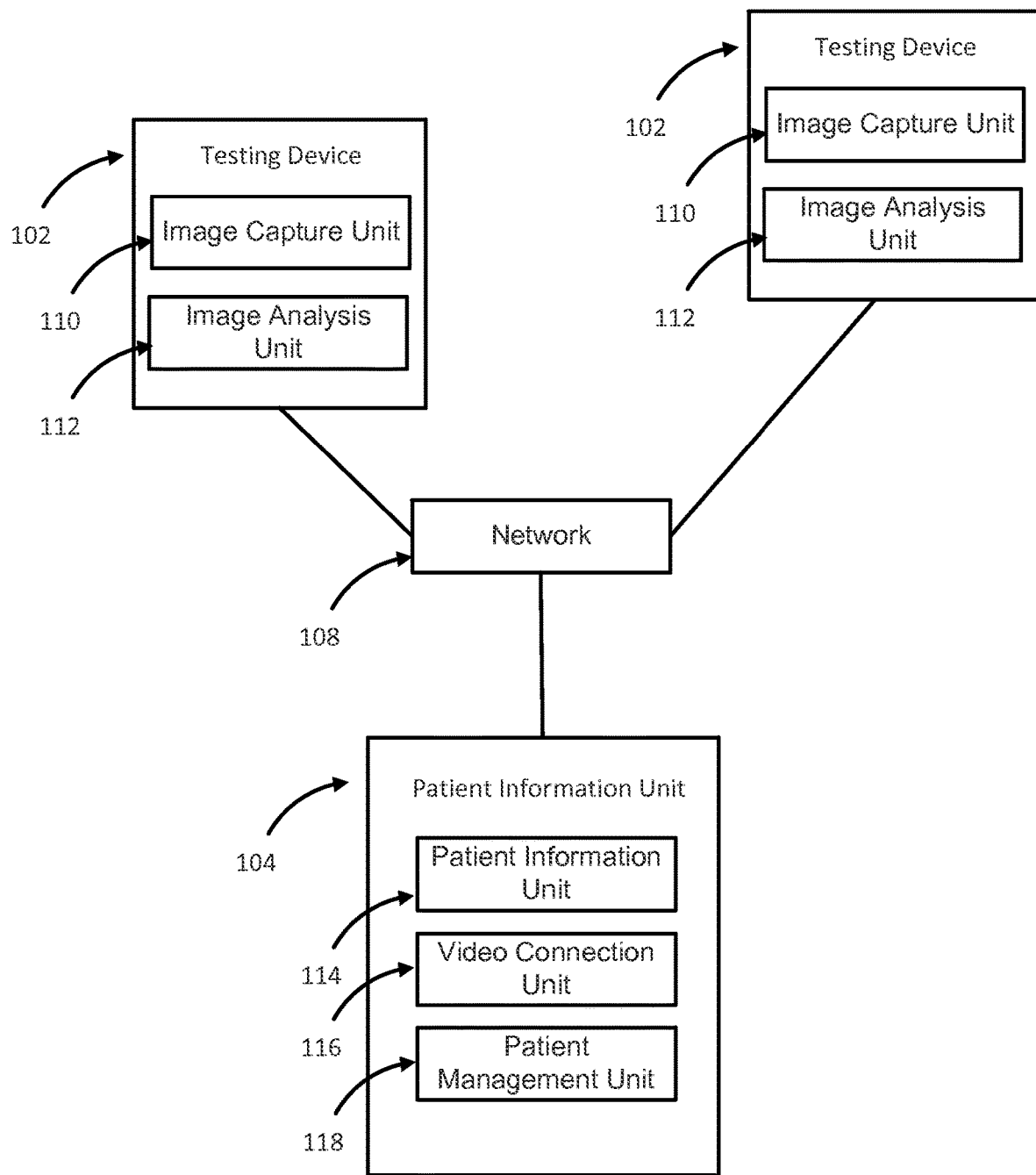
FIG. 1 depicts a block diagram of a medication monitoring system suitable for use with the methods and systems consistent with the present invention.

FIG. 1 depicts a block diagram of a medication monitoring system 100 suitable for use with the methods and systems consistent with the present invention. The medication monitoring system 100 includes a client device 102, a patient information unit 104 and a remote device 106 connected to one another via a network 108. The network is of the type suitable for connecting the client device 102, patient information unit 104 and remote device 106 such as a circuit-switched network or a packet-switched network. Also, the network 108 may include a number of different networks, such as a local area network, a wide area network such as the Internet, telephone networks including telephone networks with dedicated communication links, connectionless network, and wireless networks. The client device 102 includes an image capture unit 110 and an image analysis unit 112. The image capture unit 110 may be any image capturing device such as a digital camera. The patient information unit 104 includes a patient information unit 114, video connection unit 116 and patient management unit 118.

Figure 2A:
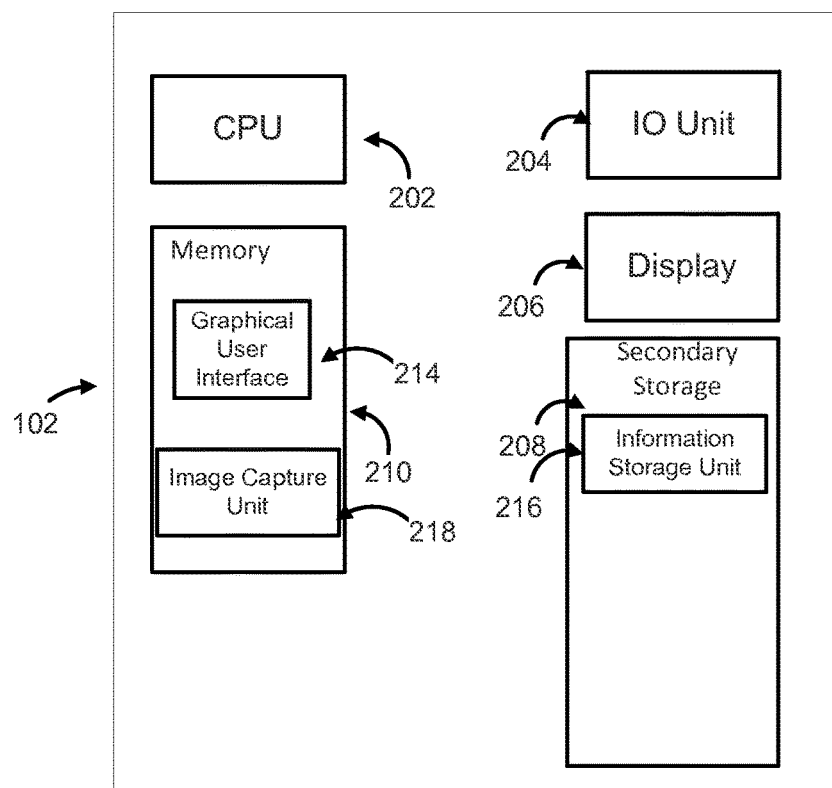
FIG. 2A shows a more detailed depiction of the client device of FIG. 1.

FIG. 2A shows a more detailed depiction of the client device 102. The client device 102 comprises a central processing unit (CPU) 202, an input output (I/O) unit 204, a display device 206, a secondary storage device 208, a memory 210 and an image capture unit 110. The client device 102 may further comprise standard input devices such as a keyboard, a mouse, a digitizer, or a speech processing means (each not illustrated).

The client device 102's memory 210 includes a Graphical User Interface (GUI) 212 which is used to gather information from a user via the display device 206 and I/O unit 204 as described herein. The GUI 214 includes any user interface capable of being displayed on a display device 206 including, but not limited to, a web page, a display panel in an executable program, or any other interface capable of being displayed on a computer screen. The secondary storage device 208 includes an image analysis unit 216. Further, the GUI 214 may also be stored in the secondary storage unit 208. In one embodiment consistent with the present invention, the GUI 214 is displayed using commercially available hypertext markup language (HTML) viewing software such as, but not limited to, Microsoft Internet Explorer®, Google Chrome® or any other commercially available HTML viewing software.

Figure 2B:
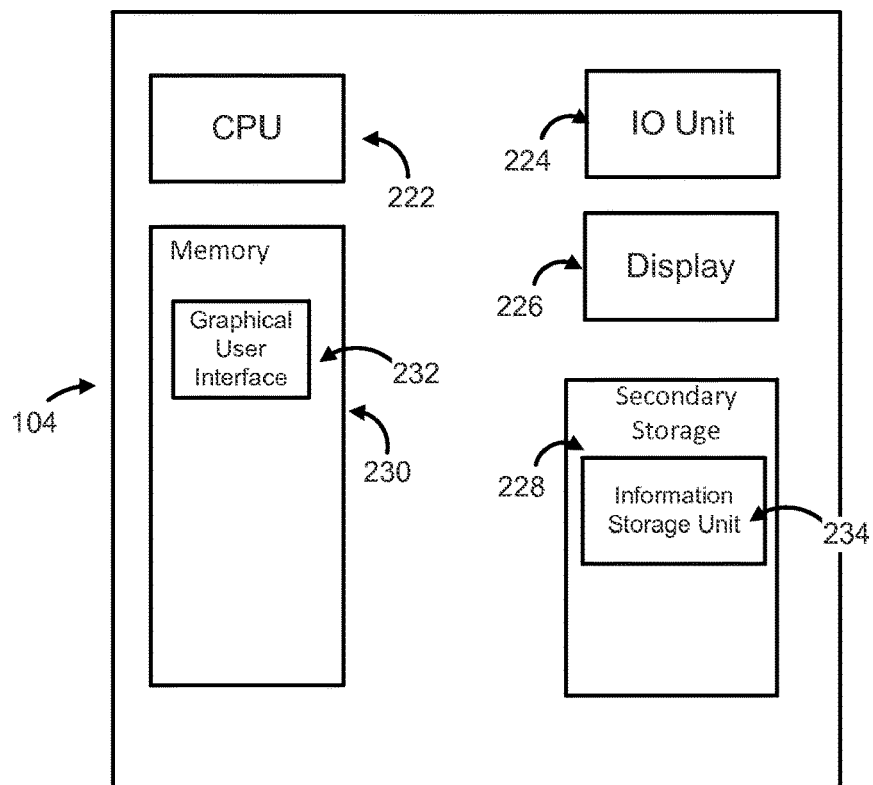
FIG. 2B shows a more detailed depiction of the patient information unit of FIG. 1.

FIG. 2B shows a more detailed depiction of the patient information unit 104. The patient information unit 104 comprises a CPU 222, a I/O unit 224, a display device 226, a secondary storage device 228, and a memory 230. Patient information unit 104 may further comprise standard input devices such as a keyboard, a mouse, a digitizer, or a speech processing means (each not illustrated). The secondary storage device 228 may include a patient information unit 234. The patient information storage unit 234 may be a database such as an Oracle, SQL or Access database.

The memory 230 in patient information unit 104 includes a GUI 232 which is used to gather information from a user via the display device 226 and I/O unit 224 as described herein. The GUI 232 includes any user interface capable of being displayed on a display device 226 including, but not limited to, a web page, a display panel in an executable program, or any other interface capable of being displayed on a computer screen. The GUI 232 may also be stored in the secondary storage unit 228. In one embodiment consistent with the present invention, the GUI 232 is displayed using commercially available HTML viewing software such as, but not limited to, Microsoft Internet Explorer®, Google Chrome® or any other commercially available HTML viewing software.

Figure 3A:
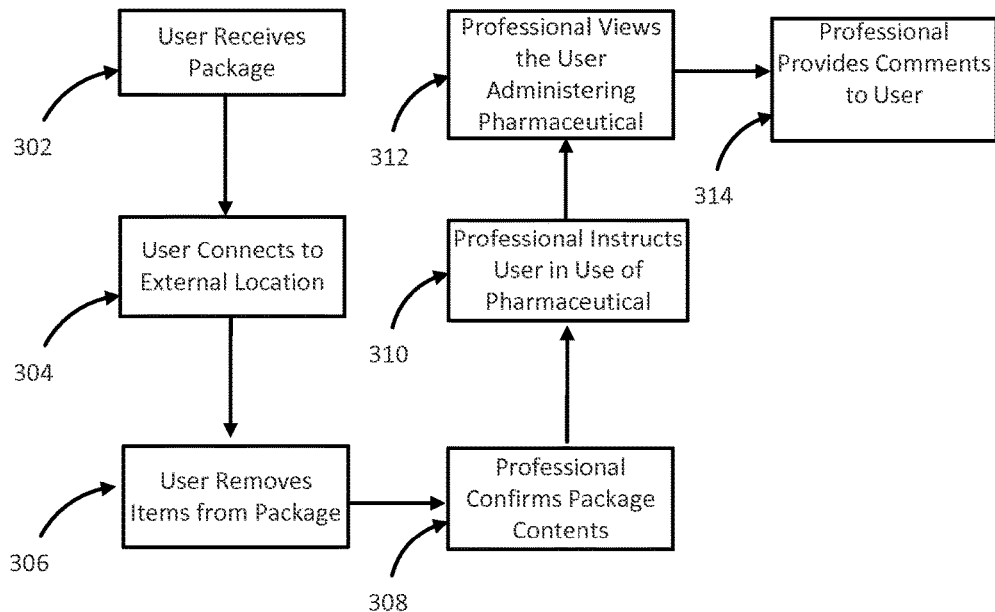
FIG. 3A depicts a process of remotely instructing a user in the use of a pharmaceutical.

FIG. 3A depicts a process of remotely instructing a user in the use of a pharmaceutical. In step 302, a user of a pharmaceutical receives a package including the pharmaceutical and dispensing equipment such as syringes. The package may include instructions for the user to connect to an external location using video communication system including, but not limited to, Skype, Facetime or Vidyo. In step 304, the user connects to the external location and initiates a video communication session via the video connection unit 114. When the user connects to the remote location via the video connection unit 114 a professional, such as a pharmacist trained in the administration of the pharmaceuticals included in the package, will discuss the correct method of taking each of the medications included in the package. Further, the professional will answer any questions posed by the user concerning the usage, storage or any other aspect of the pharmaceutical.

In step 306, the professional will have a similar package as the patient and may ask the user to remove each item in the package one item at a time with the professional, so the professional can describe each item and instruct the user in its proper use. The professional may also instruct the user in how to administer a dose of each pharmaceutical included in the package. As an illustrative example, the professional may instruct a user in the proper method to draw a pharmaceutical from a vial and inject the pharmaceutical. In step 308, the professional confirms that the correct pharmaceuticals have been sent to the user, and that the user understands when and how to administer each pharmaceutical. The professional may also confirm that the proper dosage of the pharmaceutical is taken by the user. In step 310, the professional instructs the user by demonstrating proper pharmaceutical drawing and syringe insertion on an object representing the user's body. In step 312, the professional views the user administering the medication. In step 314, the professional provides comments and observations to assist the user in properly administering the pharmaceutical.

Figure 3B:
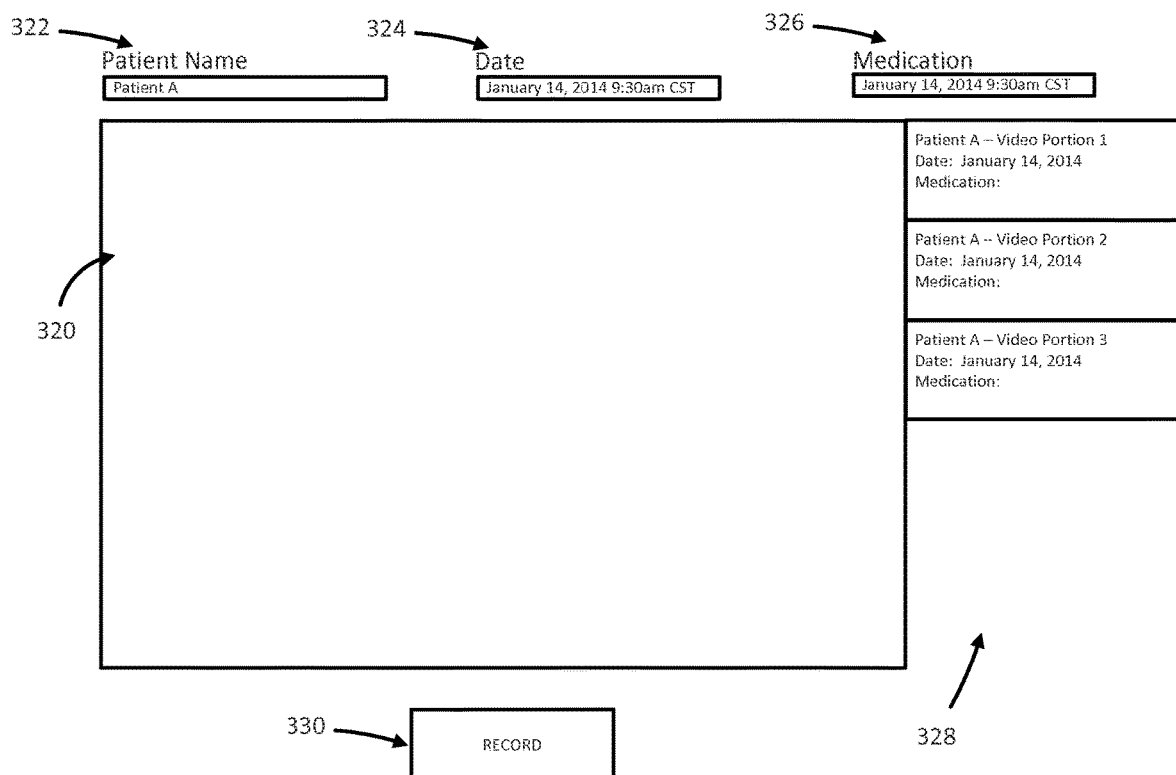
FIG. 3B depicts an embodiment of a technician interface used during a video conference.

FIG. 3B depicts an embodiment of a technician interface used during a video conference. The interface includes a video display portion 320 that is configured to display a video image of the user after the connection is established. The top portion of the interface includes a patient name gathering portion 322, a date gathering portion 324 and a medication listing portion 326. The medication listing portion 326 may allow the professional to view and select any of the medications currently prescribed to the user. In addition, the medication listing portion may allow the professional to add new medications to the list of medications prescribed to the user. A video portion 328 is positioned on one side of the video display portion 320 to allow the professional to view all recorded video associated with the user and each medication prescribed to the user. In one embodiment, when the professional selects a new medication from the medication listing portion 326, a listing of recorded video associated with the user and the medication are displayed in the video portion 328. A record button 330 allows the user to record any portion of the video stream from the video conference to the information storage unit 234.

Figure 3C:
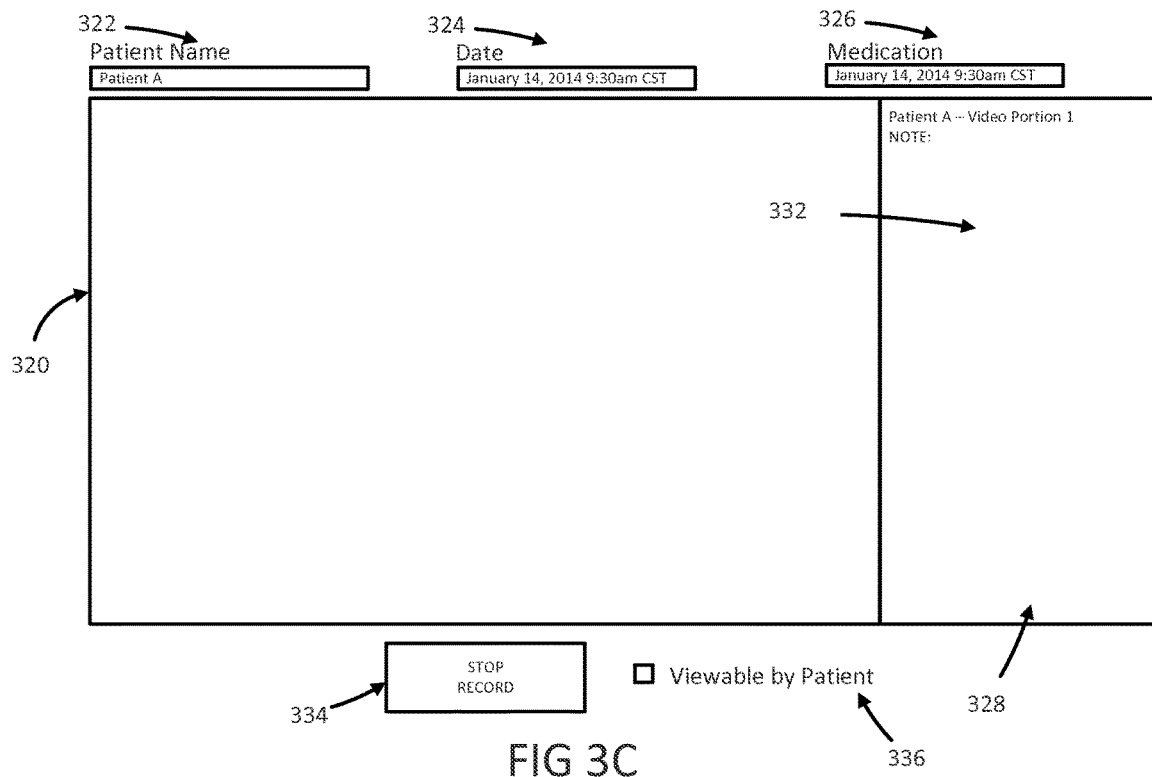
FIG. 3C depicts an embodiment of the technician interface used while a portion of the video stream is recorded.

FIG. 3C depicts an embodiment of the technician interface used while a portion of the video stream is recorded. When the record button is engaged, the video portion 320 displays a notes section 332 allowing the professional to enter observations concerning the user including observations of the user injecting and taking the medication. After the recording is stopped by the stop recording button 334, the notes are stored in the information storage unit 234 and are associated with the user, the video clip and the medication. The professional may also prevent the user from viewing the video clip by selecting the viewable by patient box 336.

The professional may record each session with the user to allow the user to replay the session at a later time. Further, the professional may provide the user with additional information in the form of documents and video segments to assist the user in the administration of the pharmaceutical. The professional may present the documents and/or video segments during the video communication session or may forward the user to a website containing the additional information. The professional may also end the call by asking the user a series of questions directed at ascertaining the user's understanding of the information covered during the video communication session. If the user fails to answer a predefined number of questions correctly, the professional may request a follow up video communication with the user to review the information covered in the video communication session and mark the follow up in the notes section 332 of the display. In one embodiment, the follow up conversation is transmitted to a scheduling system, such as Microsoft Outlook, and a reminder notice is automatically generated and transmitted to the user and the professional after a predetermined period of time has elapsed.

When the interface is executed, the video conferencing unit 116 retrieves all video stored in the information storage unit 234 that is associated with the user along with all notes associated with the user. In one embodiment, the system allows a professional to search for video portions associated with a user or with a medication. By allowing the professional to search and view video portions on a specific user or medication, the professional can quickly learn important information on a user or medication. As an illustrative example, video and note can be stored commemorating the first instance a user took a medication by a first professional. The recorded video and note can be viewed at a later time by a second professional who is unfamiliar with the patient to familiar the second professional with the user and the user's interactions and reactions to the medication.

Figure 3D:
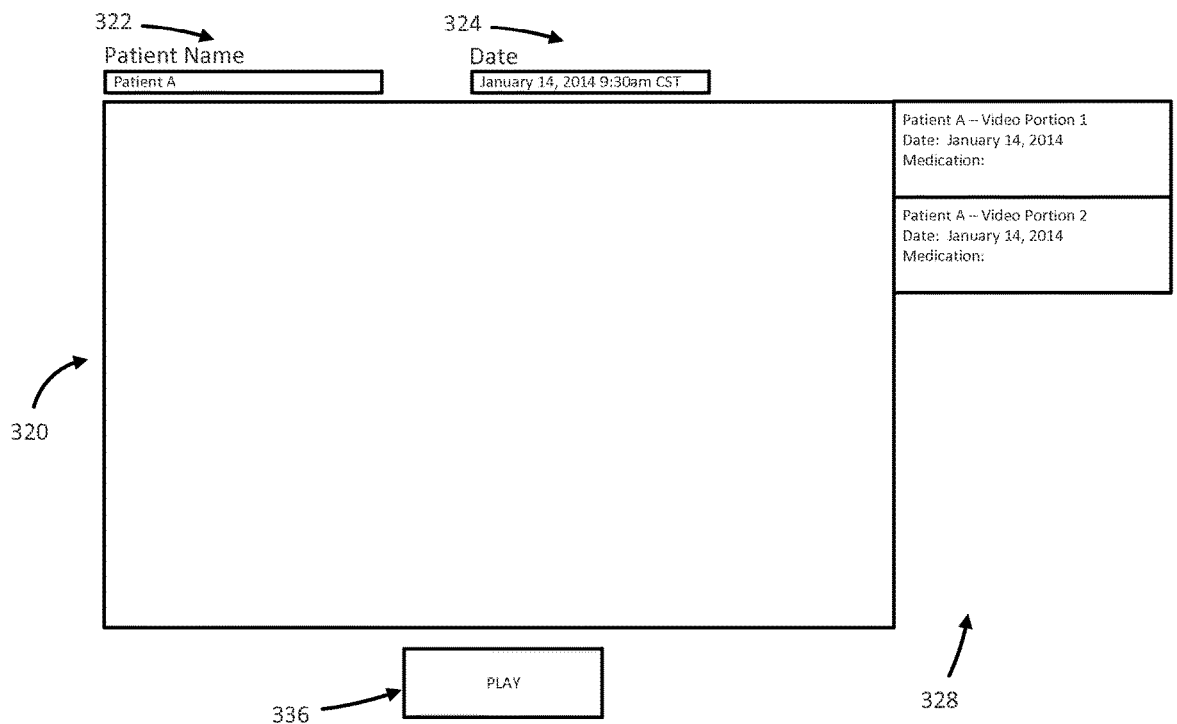
FIG. 3D depicts an embodiment of an interface used by a patient.

FIG. 3D depicts an embodiment of an interface used by a patient. The interface includes the name gathering portion 322, date portion 324 and a video selection portion 320. The video selection portion 320 displays a listing of all recorded video the patient is allowed to view. When the interface is executed, the video connection unit 116 retrieves all video portions associated with the patient and authorized for patient viewing from the information storage unit 234 and displays them in the video portion. When selected, each video portion will be displayed in the video display portion 320. In one embodiment, the patient management unit 118 may monitor the number of times a user views a video and may transmit a request for an additional consultation to the patient to confirm their understanding of the treatment. In another embodiment, the patient management unit 118 may notify a professional when a patient views a video more than a predetermined number or times. In another embodiment, the patient management unit 118 may create a notification in the video conferencing unit 116 to notify the next professional contacting the patient that the patient has viewed a video multiple times.

Figure 4:
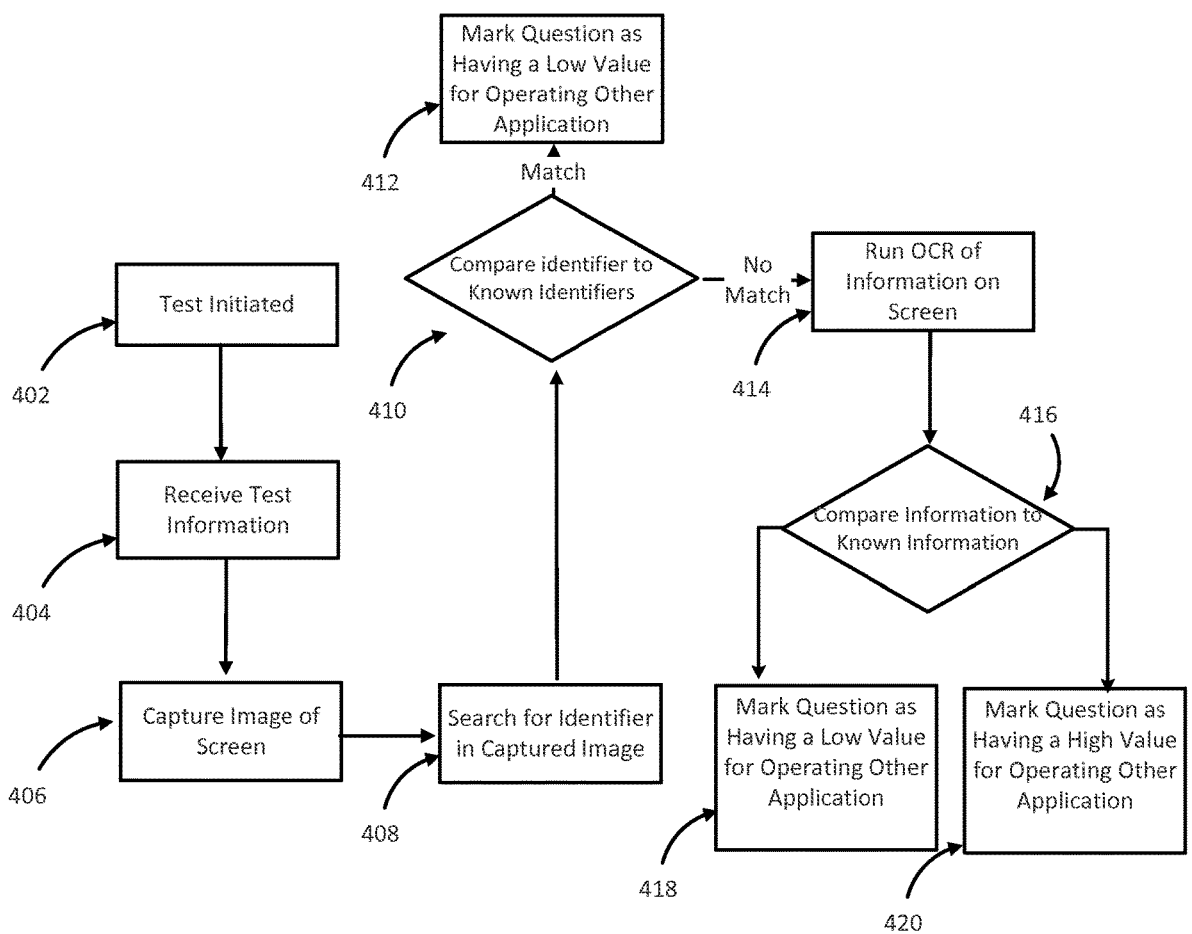
FIG. 4 depicts a schematic representation of a process executed by the image analysis unit operating on the client device.

FIG. 4 depicts a schematic representation of a process executed by the image analysis unit 112 operating on the client device 102. In step 402, the image analysis unit 104 retrieves a user identification associated with the client device 102 or the client. The identification may be a user name and password, a biometric identifier such as a finger print or a iris scan, a phone number associated with the client device, or any other attribute that can identify the user of the client device 102. In one embodiment, the image capture unit 110 may capture an image of the user's body and compare the image to a known image of the user's body to determine the identification of the user. In step 404, the image analysis unit 112 transmits a message including the client identification to the patient information unit 104 to retrieve medication and dosage information from the patient information storage unit 114. The medication and dosage information may include bar code information of the medication previously sent to the client, the type and quantity of the medication being taken by the patient, the duration between dosages for the patient, and the size and type of syringe used to inject the medication.

In step 406, the image capture unit 110 captures the image of a bar code affixed to the medication previously provided to the user. To capture the image of the bar code, the image capture unit 110 captures a digital image of the bar code which is passed to the image analysis unit 112. The image analysis unit 112 determines the bar code value by analyzing the widths and spacings in the bar code to determine the bar code value. In step 408, the image analysis unit compares the bar code value captured from the medication with the bar code value sent from the patient information storage unit 114. In step 410, if the values do not match, the image analysis unit 112 notifies the user to not take the medication and provides detailed instructions to the user on how to return the medication for replacement. The image analysis unit 112 may also transmit an incorrect medication notice to the remote device 106 to notify the sender of the medication that the incorrect medication was sent to the user.

In determining if the medication is the correct medication for the user, the image analysis unit 112 may also analyze the label affixed to the medication vial to determine the medication is the correct medication for the user. The image analysis unit 112 may perform object character recognition on an image of the label to determine the name and concentration of the medication sent to the user. The image analysis unit 112 may compare the name and dosage information with the name and dosage information provided by the patient information storage unit 114. If the information from the vial does not match the information from the patient information unit 114, the image analysis unit 112 notifies the user and the remote device 106 o the incorrect medication.

In step 412, if the medication is the correct medication, the image analysis unit 112 may retrieve a video and information on injecting the medication properly from the memory 210 and present the video to the user for viewing. In another embodiment, the image analysis unit 112 may initiate a communication connection with a pharmacist operating the remote device 106 to describe the appropriate method of injecting the medication. The communication connection may be established using any known communication method including a cellular phone call, or by a video conferencing session using video conferencing software such as Skype or Facetime. In one embodiment, the communications between the pharmacist is recorded and stored in the patent information storage unit 104 and is associated with the patient information. The image analysis unit 112 may provide an interface where the user retrieves the stored video for later viewing.

In step 414, the image analysis unit 112 retrieves an image of the vial holding the medication to determine the level of the liquid in the vial. The image analysis unit 112 may instruct the user to capture an image of the vial using a digital camera in the client device. In step 416, the image analysis unit 112 determines the level of the liquid in the vial based on the captured image. To determine the level, the image analysis unit 112 identifies the outline of the vial using known pixel analysis techniques such as Canny edge detection or SUSAN edge detection or any other known edge detection technique, and measures the distance from the a known reference point, such as the top of the vial to the top surface of the liquid level. The image analysis unit 112 can then determine the volume remaining in the vial using the dimensions in the vial that are retrieved from the patient information storage unit 114. In addition, the image analysis unit 112 identifies the top level of the liquid in the vial using the same or similar edge detection techniques. In the event the level in the vial is below a threshold value, the image analysis unit 112 may notify the remote device 106 that a refill of the medication is required. The image analysis unit 112 may notify the remote device 106 using any known messaging method including SMS messaging, e-mail, connecting to an order entry system via an ODBC connection or any other method of automatically ordering medication.

In step 418, the image analysis unit 112 notifies the user to draw a specific dosage from the vial into a syringe. In step 420, the image analysis unit requests the user capture an image of the syringe filled with the medication. In step 422, the image analysis unit 112 determines the level of liquid in the syringe and the dosage amount using the edge detection techniques described previously. The image analysis unit 112 may analyze the liquid level indicator markings on the side of the syringe and compare the proximity of the liquid level to the level indicator markings on the side of the syringe to determine the level of the medication in the syringe.

The image analysis unit 112 may also analyze the image of the syringe for proper placement to determine the liquid level shown in the image is accurate. As an illustrative example, the image analysis unit 112 may determine the angle between the edge of the syringe and the liquid level line to determine if the syringe is tiled while the image was taken. If the syringe is tilted, the image analysis unit 112 recalculates the liquid volume in the syringe using the known dimensions of the syringe that are stored in the patient information storage unit 114. In step 324, the image analysis unit 112 compares the dosage in the syringe with the prescribed dosage from the patient information system 114. If the dosage in the syringe is outside a dosage threshold, the image analysis unit 112 notifies the user to redraw the dosage in to the syringe. In step 326, if the dosage is within the predetermined dosage threshold, the image analysis unit 112 notifies the user to inject the dosage.

In one embodiment, the image analysis unit 112 records the time and type of each medication taken by the user. When the user requests the next dosage of medication be taken, the image analysis unit 112 determines if the correct interval has expired for the user to take the next dose. The image analysis unit 112 may provide a user interface such as a clock showing the time remaining before the next dose may be taken, or may provide an audible alarm notifying the patient when the next dosage is due to be taken.

Figure 5:
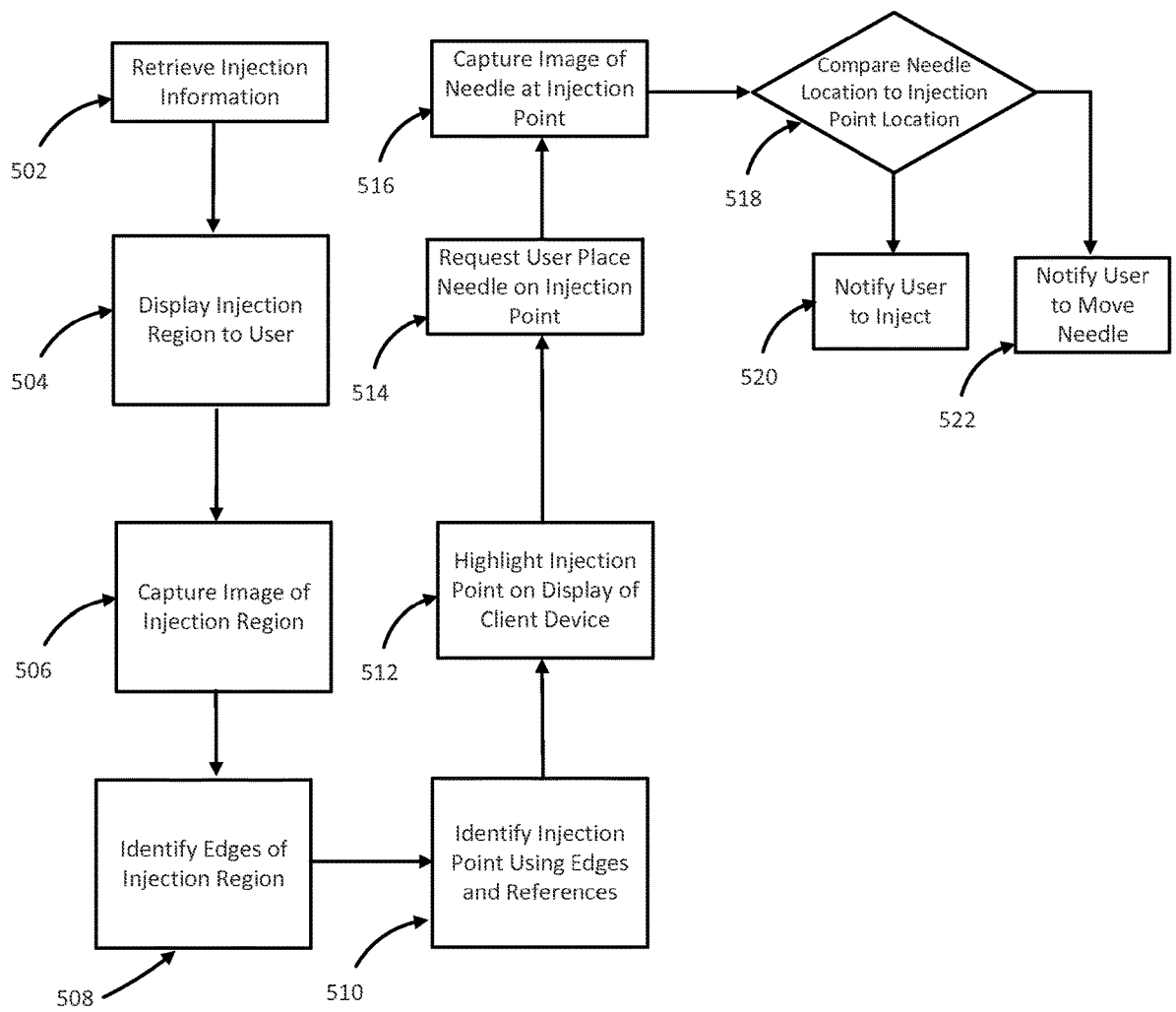
FIG. 5 depicts a schematic representation of a process executed by the image analysis unit.

FIG. 5 depicts a schematic representation of a process executed by the image analysis unit 112. In step 502, the image analysis unit 112 retrieves the injection information associated with a user and with a medication associated with the user from the patient information storage unit 114. In step 504, the image analysis unit 112 displays the area of the body where the user should inject the medication. In step 506, the image analysis unit 112 captures an image of the injection region on the user's body. In step 508, the image analysis unit 112 identifies the edges of the injection region using the edge detection techniques previously discussed. The edges of the region may be identified by first identifying an edge of the user's body, such as the edge of an arm, and measuring a predefined distance from the edge. The image analysis unit 112 may request the user place an item of a known size, such as a coin, in the image to set a distance scale for the image.

In step 510, the image analysis unit 112 identifies the location of the injection point on the image. The image analysis unit 112 may determine the injection point using a distance from an identified edge, such as the side of an arm, to determine where the needle should be injected. In step 512, the image analysis unit 112 high lights the location of the injection point on the image of the user's body. In step 514, the image analysis unit 112 requests the user place the needle of the syringe at the injection location. In step 516, the image analysis unit 112 captures an image of the needle at the injection location. In step 518, the image analysis unit 112 compares the location of the needle in the captured image to the calculated injection location. In step 520, if the needle is in the proper injection location, the image analysis unit 112 requests the user inject the needle. In step 522, if the needle is not in the proper location, the image analysis unit 112 instructs the user to move the needle to the proper location. The image analysis unit 112 may also confirm the needle is positioned at the proper angle for insertion into a vein.

FIG. 6 depicts a schematic representation of a process performed by the patient information unit 104. In step 602, the video connection unit 116 connects a user to a technician via a live video connection using any of the previously methods of establishing a video connection. In step 604, a trained technician retrieves information from a user connected via the video connection. The information may include, but is not limited t the patient's name, date of birth.

It is to be understood that both the foregoing general description and the following detailed description are exemplary and are intended to provide further explanation of the invention claimed. The disclosed configuration is the preferred embodiment and is not intended to preclude functional equivalents to the various elements.

The accompanying drawings, which are incorporated in and constitute part of this specification, are included to illustrate and provide a further understanding of the invention. Together with the description, the drawings serve to explain the principles of the invention.

What is claimed is:

1. A method of monitoring and dispensing patient information relating to use and consumption of medication, the method comprising the steps of:
   communicatively coupling a first device with a second device, at least one of the first device and the second device including a processor, a memory and a patient monitoring unit;
   providing a technician user interface on one of the first device and the second device, the technician user interface including a video display portion configured to display a video image of a user after communicatively coupling the first device with the second device, the technician user interface portion including a medication listing portion to view medications prescribed to the user, and the technician user interface portion including a video portion to view recorded video associated with at least one of the user and preparation and administration of each medication prescribed to the user;
   transmitting live images from the first device to the second device;
   analyzing the content of the live images to identify at least one of a biometric attribute of the user and a bar code on a medication container in a captured image from the live images;
   providing the user with at least one of injection information, medication information and dosage information via at least one of the video display portion and the video portion of the technician user interface; and
   further analyzing the content of the live images to determine the user's compliance with the at least one of injection information, medication information and dosage information provided to the user.

2. The method of monitoring and dispensing patient information of claim 1 wherein analyzing the content of the live image includes determining the contents of the container based on the bar code.

3. The method of monitoring and dispensing patient information of claim 1 wherein a video is streamed from the first device to the second device if content of the medication container are associated with the user.

4. The method of monitoring and dispensing patient information of claim 3 wherein the video includes instructions on how to properly administer the contents of the medication container.

5. A medication monitoring system including a patient information unit having a processor, a memory and a patient monitoring unit and a program executing in the memory executing the steps of:
   transmitting live images from a first device to a second device;
   configuring a technician user interface on one of the first device and the second device, the technician user interface including a video display portion configured to display a video image of a user after communicatively coupling the first device with the second device, the technician user interface portion including a medication listing portion to view medications prescribed to the user, and the technician user interface portion including a video portion to view recorded video associated with at least one of the user and each medication prescribed to the user;
   analyzing the content of a captured image from the live images to identify at least one biometric attribute of a user in the captured image and at least one bar code on a container in the captured image;
   determining whether the bar code is associated with at least one biometric attribute; notifying the user whether to consume a content of the container based on the association of the bar code with the at least one biometric attribute;
   using the technician user interface to provide information to the user on the proper method of preparing the content of the container for consumption, via at least one of the video display portion and the video portion;
   analyzing the content of the live images and notifying the user to determine at least one of whether the user has prepared the contents of the container for consumption or the user's compliance with the provided information.

6. The medication monitoring system of claim 5 wherein the information provided to the user includes a video depicting the preparation of the contents in the container for consumption.

7. The medication monitoring system of claim 5 including the steps of providing instructions to the user relating to the proper administration of the contents of the container.

8. The medication monitoring system of claim 7 including the step of analyzing the content of the live images to determine if the user is properly administering the contents of the container.

9. The medication monitoring system of claim 8 including the step of notifying the user if the user is not properly administering the contents of the container.

10. The medication monitoring system of claim 9 wherein the notification includes providing information relating to correction actions the user can take to properly administer the contents of the container.

11. The medication monitoring system of claim 8 wherein the contents of the container are a liquid medication.

12. The medication monitoring system of claim 11 wherein the contents of the container are administered using a syringe.

13. The medication monitoring system of claim 12 wherein the medication must be administered to a specific location of the body.

14. The medication monitoring system of claim 13 wherein the step of analyzing the content of the live images to determine if the user is properly administering the contents of the container includes determining if the user is administering the liquid to the correct location of the body.

15. A method of monitoring and dispensing patient information relating to use and consumption of medication, the method comprising the steps of:
   configuring a technician user interface on one of a first device and a second device, the technician user interface including a video display portion configured to display a video image of a user after communicatively coupling the first device with the second device, the technician user interface portion including a medication listing portion to view medications prescribed to the user, and the technician user interface portion including a video portion to view recorded video associated with at least one of the user and each medication prescribed to the user;
   transmitting live images from the first device to the second device;
   analyzing the content of a captured image from the live images to identify at least one biometric attribute of a user in the captured image and at least one bar code on a container in the captured image;
   determining whether the bar code is associated with at least one biometric attribute; notifying the user whether to consume a content of the container based on the association of the bar code with the at least one biometric attribute;

using the technician user interface to provide information to the user on the proper method of preparing the content of the container for consumption, via at least one of the video display portion and the video portion;

analyzing the content of the live images and notifying the user to determine at least one of whether the user has prepared the contents of the container for consumption or the user's compliance with the provided information.

16. The method of monitoring and dispensing patient information of claim 15 further including the step of notifying the user if the user is not properly administering the contents of the container.

17. The method of monitoring and dispensing patient information of claim 16 wherein the notification includes providing information relating to correction actions the user can take to properly administer the contents of the container.

18. The method of monitoring and dispensing patient information of claim 16 wherein the contents of the container are a liquid medication.

19. The method of monitoring and dispensing patient information of claim 16 wherein the contents of the container are administered using a syringe.

20. The medication monitoring system of claim 15 wherein the step of analyzing the content of the live images to determine if the user is properly administering the contents of the container includes determining if the user is administering the liquid to the correct location of the body.

* * * * *